(12) United States Patent
Van Rooyen et al.

(10) Patent No.: US 10,046,549 B2
(45) Date of Patent: Aug. 14, 2018

(54) METHOD AND APPARATUS FOR MANUFACTURING A CAPSULE

(71) Applicant: COMBOCAP, INC., New York, NY (US)

(72) Inventors: Jacques Van Rooyen, Cape Town (ZA); Duncan E. B. Miller, Cape Town (ZA)

(73) Assignee: COMBOCAP, INC., New York, NY (US)

( * ) Notice: Subject to any disclaimer, the term of this patent is extended or adjusted under 35 U.S.C. 154(b) by 841 days.

(21) Appl. No.: 13/797,294

(22) Filed: Mar. 12, 2013

(65) Prior Publication Data

US 2013/0186561 A1   Jul. 25, 2013

Related U.S. Application Data

(63) Continuation of application No. PCT/IB2012/055374, filed on Oct. 5, 2012.

(30) Foreign Application Priority Data

Oct. 6, 2011 (ZA) .................................. 2011/07330

(51) Int. Cl.
  *A61J 3/07* (2006.01)
  *B32B 38/18* (2006.01)
  *A61K 9/48* (2006.01)

(52) U.S. Cl.
  CPC ............... *B32B 38/18* (2013.01); *A61J 3/071* (2013.01); *A61J 3/072* (2013.01); *A61K 9/4808* (2013.01);
  (Continued)

(58) Field of Classification Search
  CPC .. B32B 38/18; B32B 38/14; A61J 3/07; A61J 3/071; A61J 3/072; A61J 3/074;
  (Continued)

(56) References Cited

U.S. PATENT DOCUMENTS

| 961,936 A | 6/1910 | Colton et al. |
| 1,510,260 A * | 9/1924 | Cyrenius ................. A61J 3/071 |
| | | 206/508 |

(Continued)

FOREIGN PATENT DOCUMENTS

| CA | 763203 A | 7/1967 |
| CA | 781906 A | 4/1968 |

(Continued)

OTHER PUBLICATIONS

International Search Report dated Mar. 22, 2013, for PCT Patent Application No. PCT/IB2012/055372 filed on Oct. 5, 2012, four pages.

(Continued)

*Primary Examiner* — Hemant M Desai
*Assistant Examiner* — Eduardo R Ferrero
(74) *Attorney, Agent, or Firm* — Morrison & Foerster LLP

(57) ABSTRACT

A method of manufacturing a capsule 12 for holding a substance 14 including providing a capsule body 2 having a closed end 5, an opposed open end 6 and a predetermined length defined between the ends 5, 6; providing a diaphragm 4 having a closed end 7, an opposed open end 8 and a predetermined length defined between the ends 7, 8; partially filling the body 2 with substance 14; inserting the closed end 7 of the diaphragm 4 into the open end 6 of the body 2 such that regions of the body 2 and the diaphragm 4 overlap one another with the open ends of the capsule body 2 and the diaphragm 4 being flush, thereby closing off the open end 6 of the body 2 and defining a chamber 104 within which the substance 14 is held; and heat welding the flush ends of the body 2 and the diaphragm 4 to one another to hermetically seal the chamber 104.

21 Claims, 9 Drawing Sheets

US 10,046,549 B2

Page 2

(52) U.S. Cl.
CPC .................. *A61J 3/07* (2013.01); *A61J 3/074* (2013.01); *A61K 9/48* (2013.01)

(58) Field of Classification Search
CPC ......... A61J 3/077; A61K 9/50; A61K 9/4833; A61K 9/48; B01D 65/00; B65B 3/027; B65B 7/2878; B65B 2230/02
USPC ....... 424/457, 453; 53/329.2, 281, 471, 478, 53/329.3, 239, 286; 432/225, 231; 156/146, 423, 285, 293, 262
See application file for complete search history.

(56) References Cited

U.S. PATENT DOCUMENTS

| | | | |
|---|---|---|---|
| 1,861,047 A | 5/1932 | Colton | |
| 2,584,622 A * | 2/1952 | Scherer | A61J 3/07 264/153 |
| 2,738,827 A | 3/1956 | Roll | |
| 2,936,493 A | 5/1960 | Scherer | |
| 3,186,910 A | 6/1965 | Glassman | |
| 3,200,556 A | 8/1965 | Ackley | |
| 3,228,789 A | 1/1966 | Glassman | |
| 3,324,902 A * | 6/1967 | Lense | A61J 3/074 141/1 |
| 3,518,340 A * | 6/1970 | Raper | A61J 3/071 128/833 |
| 3,538,677 A | 11/1970 | Amoroso et al. | |
| 3,886,940 A | 6/1975 | Hunger | |
| 3,893,278 A | 7/1975 | Lewis | |
| 3,927,195 A * | 12/1975 | Messora | A61J 3/071 206/528 |
| 3,978,640 A * | 9/1976 | Crossley | A61J 3/07 53/282 |
| 4,007,942 A | 2/1977 | Hofliger | |
| 4,089,152 A | 5/1978 | Zanasi | |
| 4,196,565 A | 4/1980 | Bodenmann et al. | |
| 4,231,211 A | 11/1980 | Strampfer et al. | |
| 4,403,461 A | 9/1983 | Goutard et al. | |
| 4,450,877 A * | 5/1984 | Walker | A61J 3/074 141/1 |
| 4,522,666 A | 6/1985 | Wittwer | |
| 4,543,138 A | 9/1985 | Bollinger et al. | |
| 4,609,417 A | 9/1986 | Smith | |
| 4,627,850 A | 12/1986 | Deters et al. | |
| 4,656,066 A * | 4/1987 | Wittwer | A61J 3/071 156/305 |
| 4,659,415 A * | 4/1987 | Shimokawa | B29C 65/18 156/293 |
| 4,662,155 A | 5/1987 | Chasman | |
| 4,667,498 A * | 5/1987 | Sauter | A61J 3/071 220/8 |
| 4,724,019 A | 2/1988 | Brown et al. | |
| 4,793,119 A * | 12/1988 | Maso | A61J 3/072 53/137.2 |
| 4,793,493 A * | 12/1988 | Makiej, Jr. | A61K 9/4808 206/528 |
| 4,899,516 A | 2/1990 | Krieger et al. | |
| 4,964,262 A | 10/1990 | Moser et al. | |
| 4,991,377 A | 2/1991 | Marchesini | |
| 4,993,137 A * | 2/1991 | Muto | A61J 3/077 106/172.1 |
| 5,074,426 A | 12/1991 | Goodhart et al. | |
| 5,081,822 A | 1/1992 | Boyd et al. | |
| 5,110,597 A * | 5/1992 | Wong | A61K 9/0004 424/438 |
| 5,111,642 A * | 5/1992 | Chiari | A61J 3/074 141/71 |
| 5,188,688 A | 2/1993 | Boardman et al. | |
| 5,223,265 A * | 6/1993 | Wong | A61K 9/0004 424/453 |
| 5,460,824 A | 10/1995 | Lebrun et al. | |
| 5,507,640 A * | 4/1996 | Gilmer | B29C 44/5636 34/104 |
| 5,674,530 A * | 10/1997 | Amidon | A61K 9/0004 424/453 |
| 5,698,155 A * | 12/1997 | Grosswald | A61J 3/077 264/297.8 |
| 5,800,422 A * | 9/1998 | Dong | A61K 9/4808 424/453 |
| 5,897,874 A * | 4/1999 | Stevens | A61K 9/4808 424/451 |
| 5,938,654 A * | 8/1999 | Wong | A61K 9/0004 424/438 |
| 5,967,405 A * | 10/1999 | Hanauska | B65D 3/06 181/178 |
| 5,976,571 A * | 11/1999 | Crison | A61J 3/071 424/453 |
| 6,303,144 B1 * | 10/2001 | Omura | A61K 9/0004 424/451 |
| 7,082,738 B2 | 8/2006 | Konishi et al. | |
| 7,163,693 B1 | 1/2007 | Clarke et al. | |
| 7,523,596 B2 * | 4/2009 | Dovesi | B65B 3/003 53/167 |
| 7,645,407 B2 * | 1/2010 | Cade | A61J 3/072 264/161 |
| 7,694,497 B2 * | 4/2010 | Tagliavini | A61J 3/074 53/452 |
| 8,621,825 B2 * | 1/2014 | Schmied | A61J 3/074 53/244 |
| 9,456,987 B2 | 10/2016 | Van Rooyen et al. | |
| 2002/0098172 A1 | 7/2002 | Udell et al. | |
| 2003/0029558 A1 | 2/2003 | Hochrainer et al. | |
| 2003/0194429 A1 | 10/2003 | Miller et al. | |
| 2003/0194431 A1 | 10/2003 | Miller et al. | |
| 2004/0081689 A1 * | 4/2004 | Dunfield | A61J 3/00 424/451 |
| 2004/0170679 A1 | 9/2004 | Schurig et al. | |
| 2005/0008690 A1 * | 1/2005 | Miller | B29C 39/10 424/451 |
| 2005/0217207 A1 | 10/2005 | Konishi et al. | |
| 2006/0064943 A1 * | 3/2006 | Trebbi | A61J 3/074 53/454 |
| 2006/0159745 A1 | 7/2006 | Baksh | |
| 2006/0188607 A1 | 8/2006 | Schramm et al. | |
| 2007/0065502 A1 | 3/2007 | Baksh | |
| 2007/0087048 A1 * | 4/2007 | Abrams | A61J 3/071 424/451 |
| 2008/0102113 A1 * | 5/2008 | Rosenberg | A61K 9/4833 424/452 |
| 2008/0236106 A1 * | 10/2008 | Trebbi | A61J 3/072 53/471 |
| 2009/0162430 A1 * | 6/2009 | Mahmoud | A61K 9/4808 424/453 |
| 2009/0205748 A1 * | 8/2009 | Ansaloni | B65B 3/323 141/250 |
| 2010/0009027 A1 | 1/2010 | Cade et al. | |
| 2010/0209389 A1 * | 8/2010 | McInnes | A61J 3/071 424/85.4 |
| 2010/0212261 A1 * | 8/2010 | Boldis | A61J 3/071 53/403 |
| 2011/0088355 A1 | 4/2011 | Fulper | |
| 2012/0035528 A1 * | 2/2012 | Coppeta | A61F 9/0017 604/20 |
| 2012/0039998 A1 | 2/2012 | Valla et al. | |
| 2012/0049410 A1 | 3/2012 | Altamar et al. | |
| 2013/0233467 A1 | 9/2013 | Van Rooyen et al. | |
| 2014/0302133 A1 | 10/2014 | Van Rooyen et al. | |
| 2016/0287522 A1 * | 10/2016 | Buydts | A61J 3/072 |

FOREIGN PATENT DOCUMENTS

| | | |
|---|---|---|
| CA | 1028951 A | 4/1978 |
| DE | 27 29 007 A1 | 1/1979 |
| EP | 0 308 637 A1 | 3/1989 |
| EP | 1 459 725 A1 | 9/2004 |
| FR | 1454013 A | 8/1966 |
| FR | 2477014 A1 | 9/1981 |
| FR | 2480598 A2 | 10/1981 |
| GB | 1027779 A | 4/1966 |
| GB | 1027780 A | 4/1966 |

(56) References Cited

FOREIGN PATENT DOCUMENTS

| | | |
|---|---|---|
| GB | 2002316 A | 2/1979 |
| JP | S45359 B1 | 1/1970 |
| JP | S5029734 A | 3/1975 |
| JP | 2010-533013 A | 10/2010 |
| NL | 7610038 A | 3/1978 |
| WO | WO-94/03365 A1 | 2/1994 |
| WO | WO-2007/047371 A2 | 4/2007 |
| WO | WO-2007/047371 A3 | 4/2007 |
| WO | WO-2008/113368 A1 | 9/2008 |
| WO | WO-2013/050973 A1 | 4/2013 |

OTHER PUBLICATIONS

International Search Report dated Feb. 12, 2013, for PCT Patent Application No. PCT/IB2012/055374 filed on Oct. 5, 2012, four pages.
Written Opinion of the International Searching Authority dated Mar. 22, 2013, for PCT Patent Application No. PCT/IB2012/055372 filed on Oct. 5, 2012, five pages.
Written Opinion of the International Searching Authority dated Feb. 12, 2013, for PCT Patent Application No. PCT/IB2012/055374 filed on Oct. 5, 2012, six pages.
Capsule Size Chart by Torpac Inc. (2000). Three Total Pages.

\* cited by examiner

METHOD AND APPARATUS FOR MANUFACTURING A CAPSULE

CROSS-REFERENCE TO RELATED APPLICATIONS

This application is a continuation of International Application No. PCT/IB2012/055374 filed Oct. 5, 2012 and claims the benefit of South African Application No. 2011/07330 filed Oct. 6, 2011, the disclosures of which are incorporated herein by reference in their entirety

FIELD OF INVENTION

This invention relates to a method and apparatus for manufacturing a capsule of a type suitable for holding a substance which is required to be held in hermetic isolation. In this specification the term "non-toxic gas" must be interpreted to mean any gas which is non-toxic to a human or animal body when ingested and which specifically does not contain oxygen.

SUMMARY OF INVENTION

According to a first aspect of the invention there is provided a method for manufacturing a capsule for holding a substance which is required to be held in hermetic isolation, the method including the steps of:
providing a first capsule portion of flexible material for holding the substance, the first capsule portion having a closed end, an opposed open end and a predetermined length dimension defined between the ends thereof;
providing a second capsule portion of flexible material having a closed end, an opposed open end and a predetermined length dimension defined between the ends thereof, which is shorter than the length dimension of the first capsule portion;
at least partially filling the first capsule portion with the substance;
inserting the closed end of the second capsule portion into the open end of the first capsule portion until the open ends of the first capsule portion and the second capsule portion are aligned substantially flush with one another and such that a region of the second capsule portion overlaps a region of the first capsule portion so as to close off the open end of the first capsule portion and define a chamber within which the substance is held; and
bonding the substantially flush aligned open ends of the first capsule portion and the second capsule portion to one another, thereby to hermetically seal the chamber.

The method may include supporting the open ends of the first capsule portion and the second capsule portion while bonding the substantially flush aligned open ends of the first capsule portion and the second capsule portion to one another.

The method may include supporting inner and outer sides of the first and second capsule portions at an open end region defined adjacent the substantially flush aligned open ends of the first capsule portion and second capsule portion.

The method may include bonding the substantially flush aligned open ends of the first capsule portion and the second capsule portion to one another by applying heat and pressure to the open ends of the first and second capsule portions, so as to fuse the open ends of the capsule portions to one another.

The method may include bonding the overlapping regions of the first capsule portion and the second capsule portion to one another.

The method may include bonding the overlapping regions to one another by applying heat and pressure to the overlapping regions.

The method may include providing a gas-tight chamber in order to achieve a controlled gaseous environment within the chamber, the method including locating the first and second capsule portions within the chamber and inserting the closed end of the second capsule portion into the open end of the first capsule portion while in the chamber.

The method may include providing a non-toxic gas environment within the chamber and inserting the closed end of the second capsule portion within the first capsule portion while the capsule portions are located within the non-toxic gas environment.

The method may include applying a partial vacuum to the chamber thereby to reduce gas pressure within the chamber to a sub-atmospheric pressure when inserting the closed end of the second capsule portion into the open end of the first capsule portion.

The first capsule portion may comprise a hollow cylindrical tubular body which defines the open end and the closed end, the closed end being dome-shape.

The second capsule portion may comprise a hollow cylindrical tubular body which defines the open end and the closed end, the closed end being dome-shape.

The method may include the steps of providing a cap; at least partially filling the second capsule portion with an additional substance; and securing the cap to one of the first capsule portion and the second capsule portion so as to define an additional chamber within which the additional substance is held.

The method may include securing the cap to one of the first capsule portion and the second capsule portion in an arrangement wherein the cap closes the open end of the second capsule portion.

The first capsule portion and the second capsule portion may both be formed of digestible material rendering the capsule digestible.

The first capsule portion, the second capsule portion and the cap may be formed of digestible material, rendering the capsule digestible.

According to a second aspect of the invention there is provided an apparatus for manufacturing a capsule for holding a substance which is required to be held in hermetic isolation, the apparatus including:
first capsule receiving means including at least one first capsule receiving formation which is dimensioned and configured for receiving therein a first capsule portion of flexible material for holding the substance therein, the first capsule portion having a closed end, an opposed open end and a predetermined length dimension defined between the ends thereof;
capsule filling means including one or more nozzles for dispensing the substance, the capsule filling means being operable for at least partially filling the first capsule portion which is supported, in use, by the first capsule receiving formation;
second capsule handling means including at least one second capsule handling formation which is configured for handling a second capsule portion of flexible material having a closed end, an opposed open end and a predetermined length dimension defined between the ends thereof, which is shorter than the length dimension of the first capsule portion, the second capsule handling means being displaceable between:

a first condition wherein the second capsule handling formation of the second capsule handling means is spaced apart from the first capsule receiving formation of the first capsule receiving means; and a second condition wherein the second capsule handling formation is operable to insert a closed end of the second capsule portion handled thereby within the first capsule portion received by the first capsule receiving formation until the open ends of the first and second capsule portions are aligned substantially flush with one another and such that a region of the second capsule portion overlaps a region of the first capsule portion thereby closing off the open end of the first capsule portion so as to form an assembled capsule defining a chamber within which the substance is held; and capsule bonding means for bonding the substantially flush aligned open ends of the first capsule portion and the second capsule portion of each assembled capsule to one another, thereby to hermetically seal the chamber.

The first capsule receiving formation may be configured and dimensioned for supporting an open end region of the first capsule portion defined adjacent the open end of the first capsule portion.

The second capsule handling formation may be configured and dimensioned to be inserted through the open end of the second capsule portion for supporting an open end region of the second capsule portion defined adjacent the open end of the second capsule portion.

The capsule bonding means may be in the form of at least one capsule bonding element for applying heat and pressure to the first and second capsule portions of the assembled capsules for bonding the first and second capsule portions to one another.

The capsule bonding element may define an end engaging formation which is configured and dimensioned for engaging the substantially flush aligned open ends of the first and second capsule portions for applying heat and pressure to the open ends for bonding the open ends of the first and second capsule portions to one another.

The capsule bonding element may have a second capsule engaging formation which is configured and dimensioned for engaging an inner side of the second capsule portion for applying heat and pressure to the second capsule portion for bonding the overlapping regions of the first and second capsule portions to one another.

The apparatus may include a gas-tight chamber within which the first and second capsule portions are located when inserting the first capsule portion into the second capsule portion when forming an assembled capsule, thereby to achieve a controlled gaseous environment within the chamber.

The apparatus may include a vacuum device for applying a partial vacuum to the chamber for reducing gas pressure within the chamber to sub-atmospheric pressures.

BRIEF DESCRIPTION OF THE DRAWINGS

Further features of the invention are described hereinafter by way of a non-limiting example of the invention, with reference to and as illustrated in the accompanying diagrammatic drawings. In the drawings.

DETAILED DESCRIPTION OF THE DRAWINGS

Figure 1:
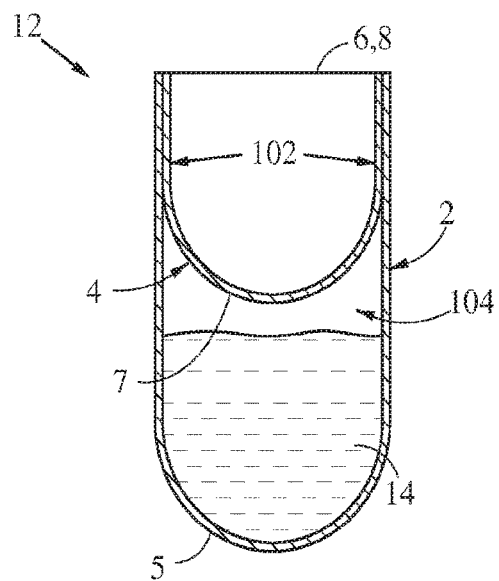
FIG. 1 shows a sectional side view of a capsule produced in accordance with the method of manufacturing a capsule, in accordance with the first aspect of the invention.

With reference to FIGS. 1 and 3 to 10 of the drawings, an apparatus in accordance with a second aspect of the invention is designated generally by the reference numeral 10. The apparatus 10 is configured for manufacturing a capsule 12 in accordance with the method for manufacturing a capsule, in accordance with a first aspect of the invention.

The capsule 12 is in the form of a digestible hard gelatine capsule for holding a substance such as, for example Omega-3 oil 14 which, when contained in a capsule, is required to be held in hermetic isolation for two main reasons. Firstly, because Omega-3 oil 14 is in a flowable liquid state and, as such, must be held in a liquid-tight chamber within the capsule. Secondly, because Omega-3 oil 14 is susceptible to degradation by oxidation when exposed to oxygen present in the atmosphere. The capsule 12 comprises, broadly, a first capsule portion in the form of a capsule body 2 and a second capsule portion in the form of a diaphragm 4. The capsule body 2 is of a flexible gelatinous material and is in the form of hollow cylindrical tubular body which defines a closed end 5 and an opposed open end 6 and which has a predetermined length dimension defined between the ends 5, 6 thereof. The diaphragm 4 is of a flexible gelatinous material having a hollow cylindrical tubular body which defines a closed end 7 and an opposed open end 8 and which has a predetermined length dimension defined between the ends 7, 8 thereof, which is shorter than the length dimension of the capsule body 2.

Figure 3:
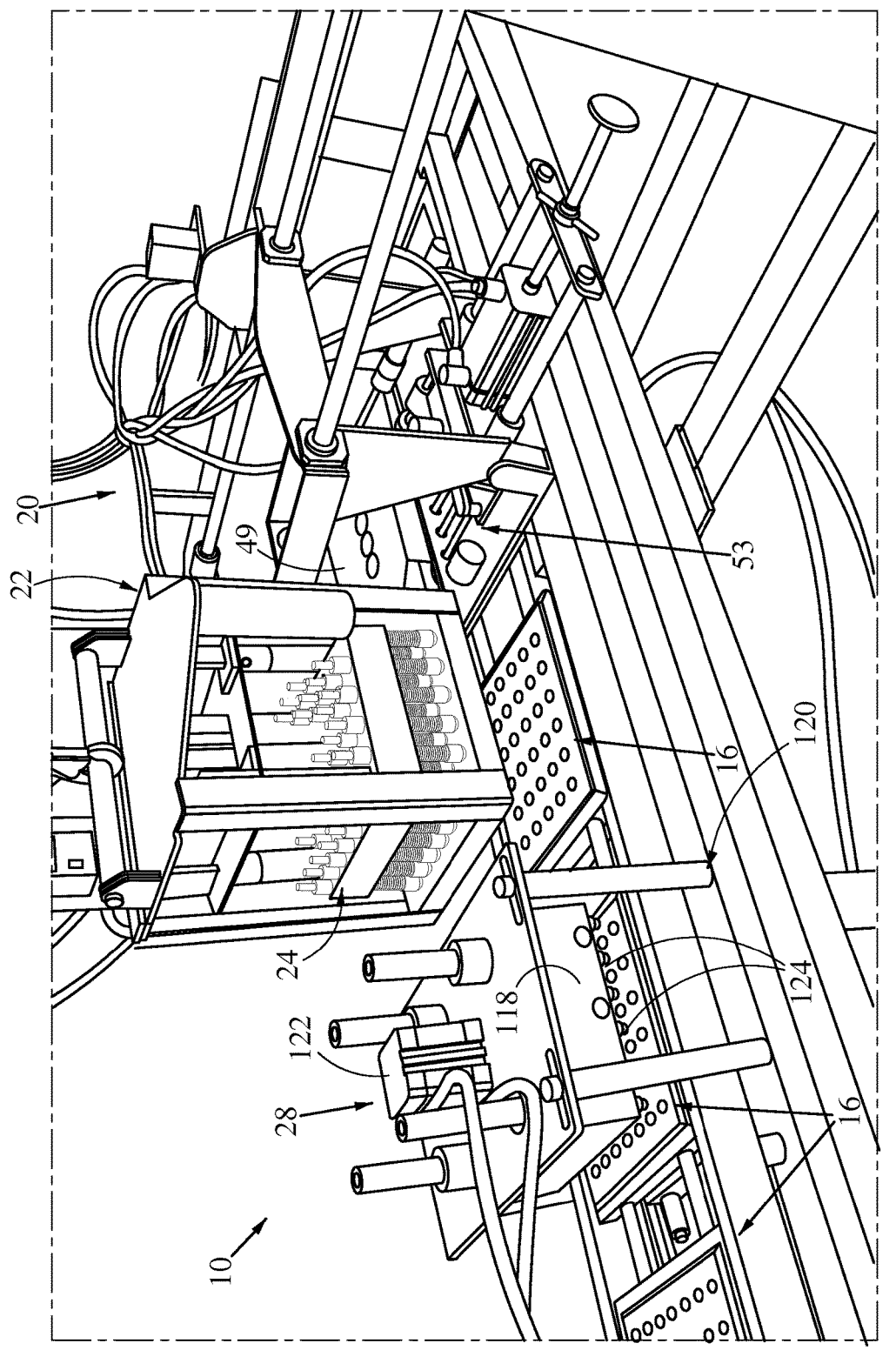
FIG. 3 shows a fragmentary perspective view of an apparatus for manufacturing a capsule, in accordance with a second aspect of the invention.

As is illustrated in FIG. 3 of the drawings, the apparatus 10 includes, broadly, first capsule receiving means in the form of a number of capsule support trays 16; a capsule filling assembly 20; a vacuum chamber assembly 22; second capsule handling means in the form of a diaphragm inserting assembly 24; and capsule bonding means in the form of a capsule bonding assembly 28.

Figure 4:
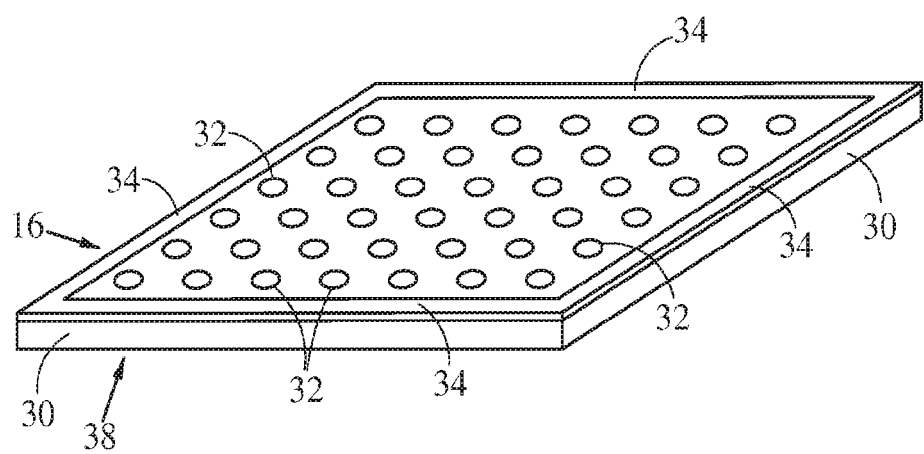
FIG. 4 shows a perspective view of a capsule support tray of the apparatus of FIG. 3.

With reference to FIGS. 3 and 4 of the drawings, each capsule support tray 16 comprises an aluminium plate 30 having forty two hollow receptacles 32 defined therein; a peripheral rubber seal 34; and forty two internal passages 36 which extend through the aluminium plate 30 from bottom end regions 38 of the aluminium plate 30 to a lowermost part of a different one of the receptacles 32, the purpose of which will be explained in more detail hereinbelow. The receptacles 32 are spaced an equal distance apart from one another and are arranged in a grid arrangement comprising six rows by seven columns. Each receptacle 32 is configured and dimensioned for receiving a capsule body 2. More specifically, each receptacle 32 is configured and dimensioned so as to support an open end region of the capsule body 2 defined adjacent the open end 6 of the capsule body 2.

Each capsule support tray 16 is displaced, in use, to various positions on the apparatus which correspond to various operational stations of the apparatus 10. More specifically, each capsule support tray 16, is displaced, in use, sequentially between: a capsule filing station, wherein the capsule support tray 16 is disposed beneath the capsule filling assembly 20; a vacuum-insertion station, wherein the capsule support tray 16 is disposed beneath the vacuum chamber assembly 22 and beneath the diaphragm inserting assembly 24; and a capsule bonding station, wherein the capsule support tray 16 is disposed beneath the capsule bonding assembly 28.

Figure 5:
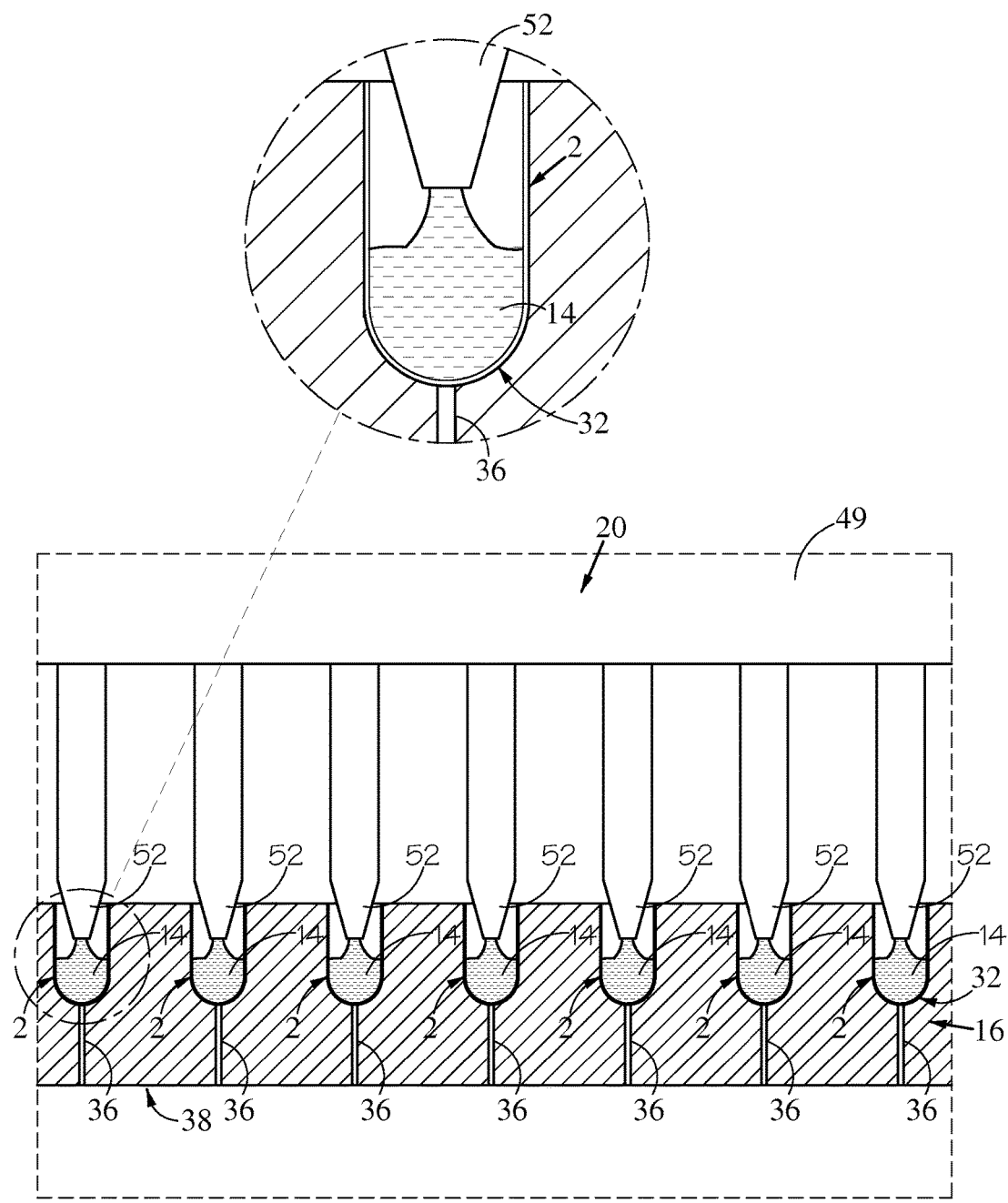
FIG. 5 shows a fragmentary sectional side view of a capsule filling assembly of the apparatus of FIG. 3.

As is illustrated in FIGS. 3 and 5 of the drawings, the capsule filling assembly 20 includes a movable capsule filling head 49 and a metered dispenser 53. The capsule filling head 49 includes seven nozzles 52 which are spaced an equal distance apart from one another and which are aligned in a row, so that the position of each nozzle 52 corresponds with a particular receptacle 32 of the aluminium plate 30 located beneath it, as shown in FIG. 5 of the drawings. The rows of nozzles 52 are sequentially moved to positions wherein the nozzles 52 are positioned above each row of the receptacles 32 of the aluminium plate 30. The metered dispenser 53 is operable to deliver a specific metered dose of Omega-3 oil 14 to each nozzle 52, for partially filling each capsule body 2 which is supported within the receptacles 32 of the capsule support tray 16.

Figure 6:
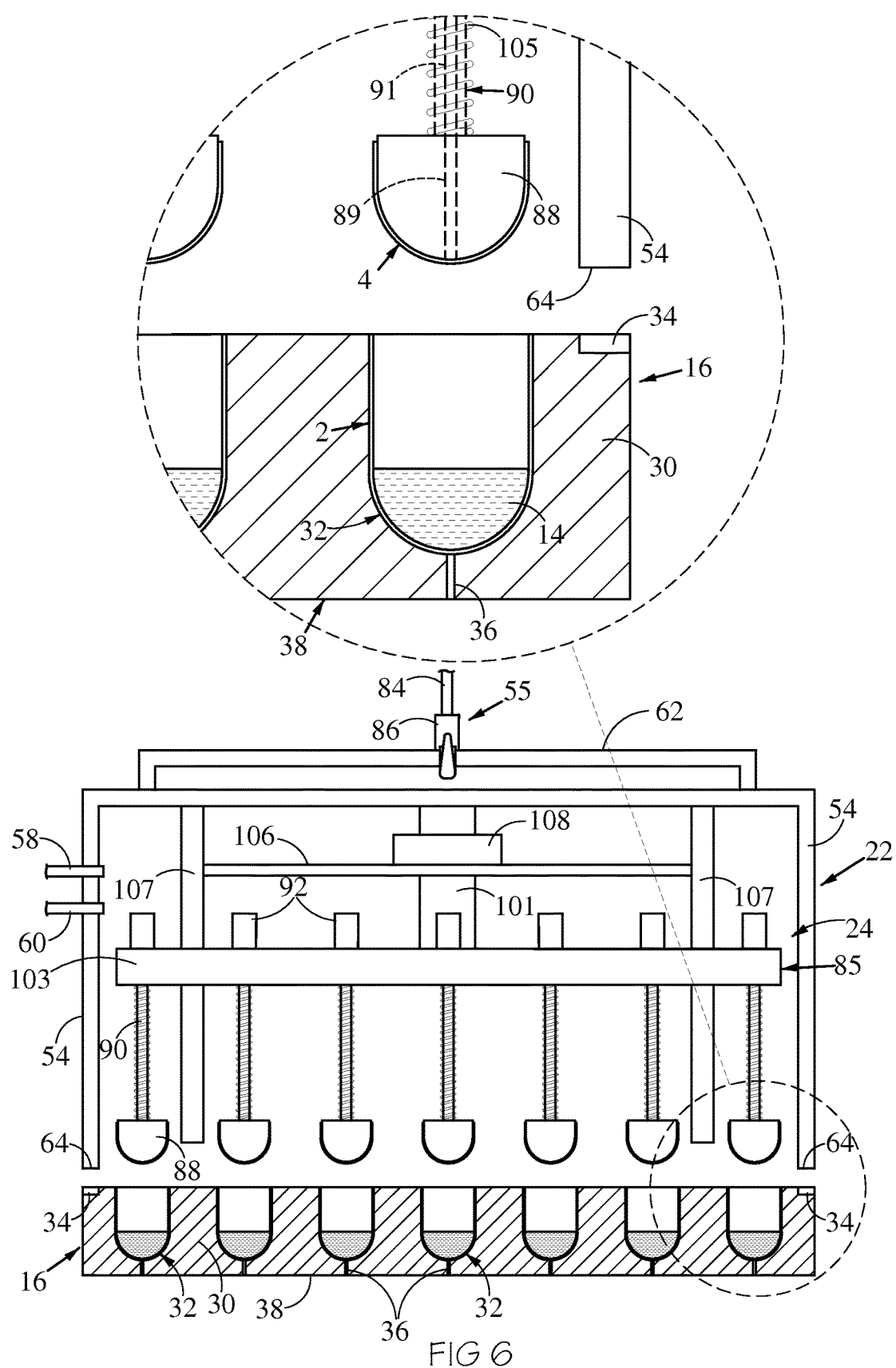
FIG. 6 shows a fragmentary sectional side view of a vacuum chamber assembly and a diaphragm inserting assembly of the apparatus of FIG. 3, both illustrated in raised positions.
Figure 7:
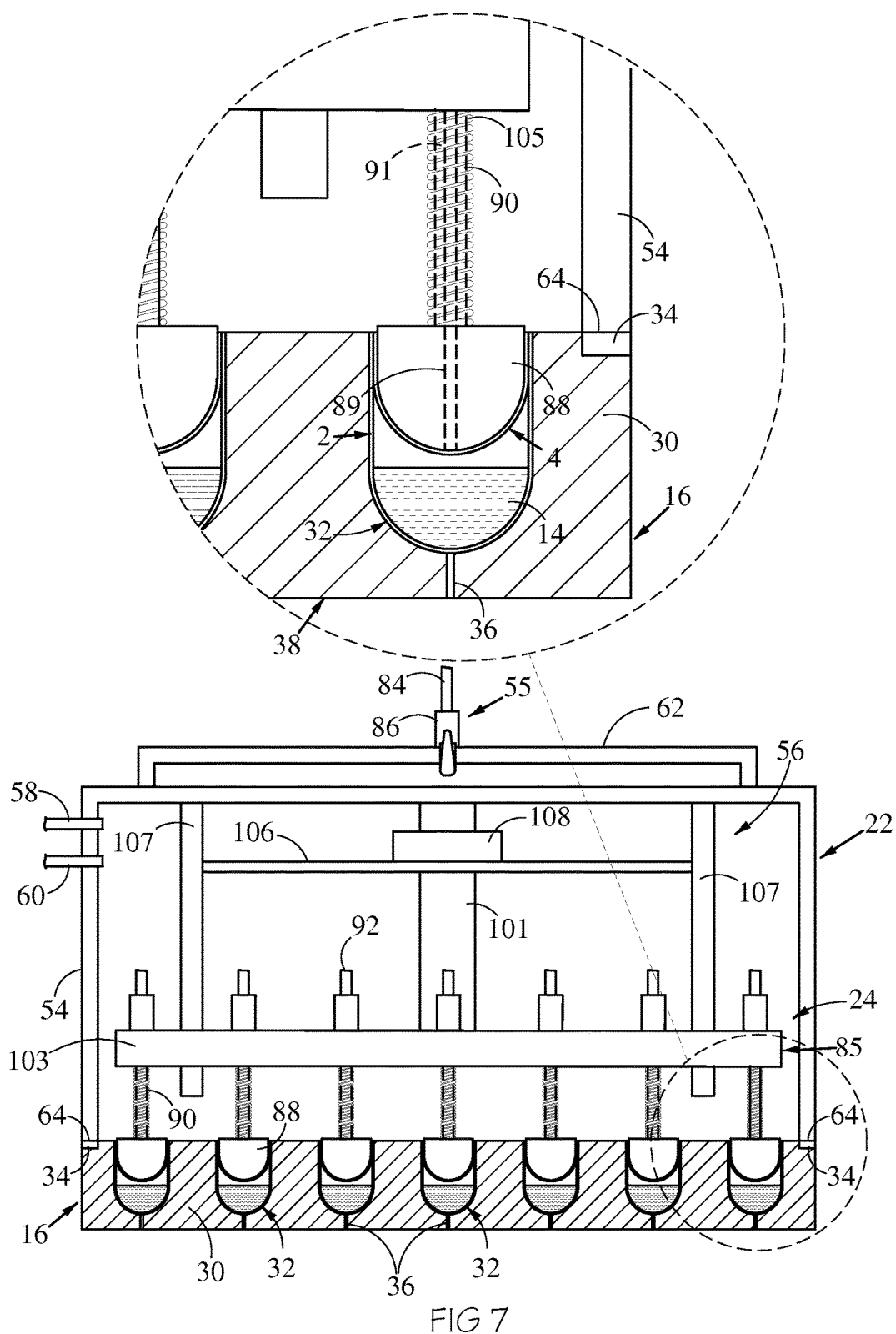
FIG. 7 shows a fragmentary sectional side view of the vacuum chamber assembly and the diaphragm inserting assembly of FIG. 6, both illustrated in lowered positions.
Figure 8:
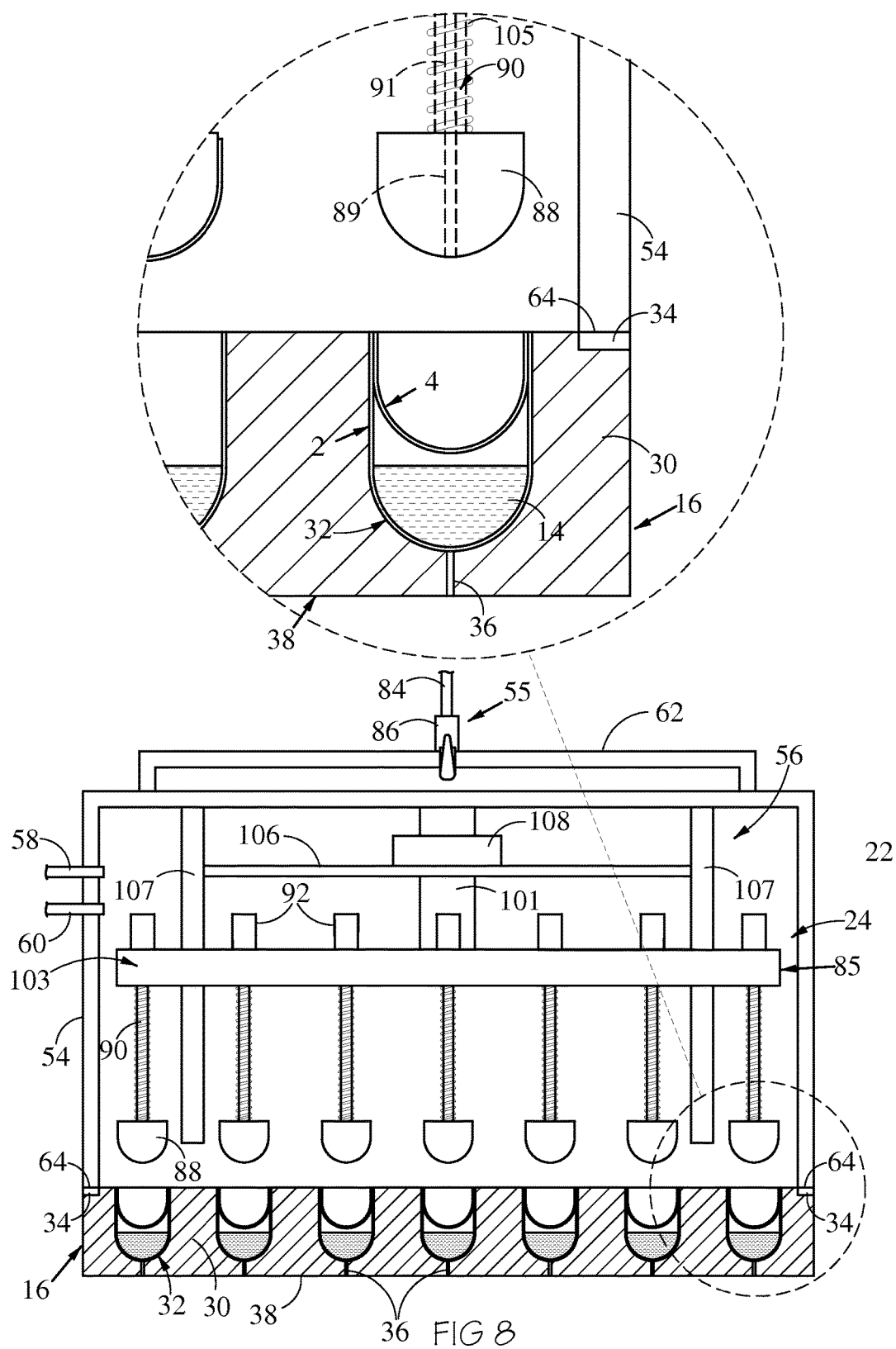
FIG. 8 shows a fragmentary sectional side view of the vacuum chamber assembly and diaphragm inserting assembly of FIG. 6, with the vacuum chamber assembly illustrated in the lowered position and the diaphragm inserting assembly illustrated in the raised position.

With reference to FIGS. 3 and 6 to 8 of the drawings, the vacuum chamber assembly 22 comprises a vacuum chamber housing 54; a vacuum chamber displacing assembly 55 for displacing the vacuum chamber housing 54; a vacuum port 58 and a nitrogen delivery port 60. The vacuum chamber housing 54 has a sealing formation 64 defined on a lower peripheral edge; and a handle formation 62 extending from the housing 54, the purpose of which will be described in more detail hereinbelow. The vacuum chamber displacing assembly 55 comprises a winch (not shown) having a steel cable 84 with a hook 86 at a free end of the steel cable 84 connected to the handle formation 62 of the housing 54. The vacuum chamber displacing assembly 55 is operable to displace the housing 54 between a raised position, as shown in FIGS. 3 and 6 of the drawings and a lowered position, as shown in FIGS. 7 and 8 of the drawings, wherein the sealing formation 64 of the housing 54 sealingly engages the rubber seal 34 of the capsule support tray 16, so as to define an internal vacuum chamber 56 which is defined between the housing 54 and the capsule support tray 16. The vacuum port 58 is connected to a vacuum pump (not shown) so as to form a partial vacuum within the vacuum chamber 56 when the vacuum pump is operated. The nitrogen delivery port 60 is connected to a source of nitrogen gas for delivering nitrogen gas to the vacuum chamber 56.

With reference to FIGS. 3 and 6 to 8 of the drawings, the diaphragm inserting assembly 24 is mounted within the housing 54 of the vacuum chamber assembly 22 and includes forty two diaphragm inserting rods 90 and a hydraulically-operated rod-displacing arrangement 85 for displacing the diaphragm inserting rods 90. Each diaphragm inserting rod 90 has a threaded end (not shown), an opposite end which is connected to a second capsule handling formation in the form of a mandrel 88; and a hollow internal passage 91 extending from the threaded end of the rod 90 to the opposite end thereof. Each mandrel 88 has a hollow central passage 89 defined therethrough and is configured for handling and supporting a diaphragm 4. More specifically, each mandrel 88 is configured and dimensioned to be inserted through an open end 8 of a diaphragm 4 so as to be received within the diaphragm 4 in a snug sliding fit, and is shaped and dimensioned to correspond to a shape and dimension of an inner side 102 of the diaphragm 2. More specifically, each mandrel 88 is dimensioned and configured for supporting the open end 8 of the diaphragm 4. The rod displacing arrangement 85 comprises four guide posts 107, a carrier plate 103; forty two springs 105 and nuts 92; an actuator plate 106 and hydraulic actuator 108; and a movable piston 101. The guide posts 107 are mounted at upper ends thereof to the housing 54 of the vacuum chamber assembly 22. The carrier plate 103 is slidably received on the guide posts 107 and has 42 equi-spaced apertures which extend therethrough, through which the diaphragm inserting rods 90 are received. Each spring 105 is received on a different one of the diaphragm inserting rods 90 and the nuts 92 are threaded onto the threaded ends of the diaphragm inserting rods 90, as illustrated in FIGS. 6 to 8 of the drawings. The hydraulic actuator 108 is operable to displace the piston 101 for displacing the carrier plate 103 and the diaphragm inserting rods 90 mounted thereto, for reasons which will be explained in more detail hereinbelow.

In use, the vacuum chamber displacing assembly 55 displaces the housing 54 into its lowered position, as shown in FIGS. 7 and 8 of the drawings, wherein the sealing formation 64 of the housing 54 sealingly engages the rubber seal 34 of the capsule support tray 16. The vacuum pump is activated so as to draw air out of the vacuum chamber 56 so as to form a partial vacuum within the vacuum chamber 56 so as to reduce internal pressure within the vacuum chamber 56 to a pressure of between 10 kPa to 70 kPa. Nitrogen gas is then introduced into the vacuum chamber 56 via the nitrogen delivery port 60 to increase the internal pressure within the vacuum chamber 56 to a pressure of 20 kPa to 90 kPa, which particularly is below atmospheric pressure for reasons which will be explained in more detail hereinbelow.

In use, the rod displacing arrangement 85 is operable to displace the piston 101 for displacing the inserting rods 90 and the mandrels 88 between a first condition, as shown in FIG. 6 of the drawings, wherein the mandrels 88 are spaced apart from the receptacles 32 of the capsule support trays 16 and a second condition, shown in FIG. 7 of the drawings, wherein the mandrels 88 are operable to insert a closed end 7 of each diaphragm 4 supported thereon, within a different one of the capsule bodies 2, supported by the receptacles 32 of the capsule support trays 16, until the open ends 6, 8 of the capsule body 2 and the diaphragm 4 are aligned substantially flush with one another, and such that a region of each diaphragm 4 overlaps a region of a different one of the capsule bodies 2, thereby closing off the open ends 6 of the capsule body 2 thereby to form an assembled capsule 12 defining a chamber 104 in which the Omega-3 oil 14 is held.

It will be appreciated that the receptacles 32 and the mandrels 88 together support the open ends 6, 8 of the capsule body 2 and the diaphragm 4 and inner and outer sides of overlapping region of the capsule body 2 and the diaphragm 4, as shown in FIG. 7 of the drawings, during insertion of the closed end 7 of the diaphragm 4 into the open end 6 of the capsule body 2. The provision of support for an outer side of the capsule body 2 and an inner side of the diaphragm 4 and particularly for the open ends 6, 8, is advantageous during insertion, as this ensures that the open ends 6, 8 of the capsule body 2 and the diaphragm 4 do not distort and/or change shape when the closed end 7 of the diaphragm 4 is inserted within the capsule body 2. It will be understood in this regard that gelatine capsules are particularly fragile and easily distort and/or rupture when relatively small forces are applied thereto. Any distortion to the shape of the capsule body 2 will also hamper removal of the capsule body 2 from the receptacle 32.

Figure 9:
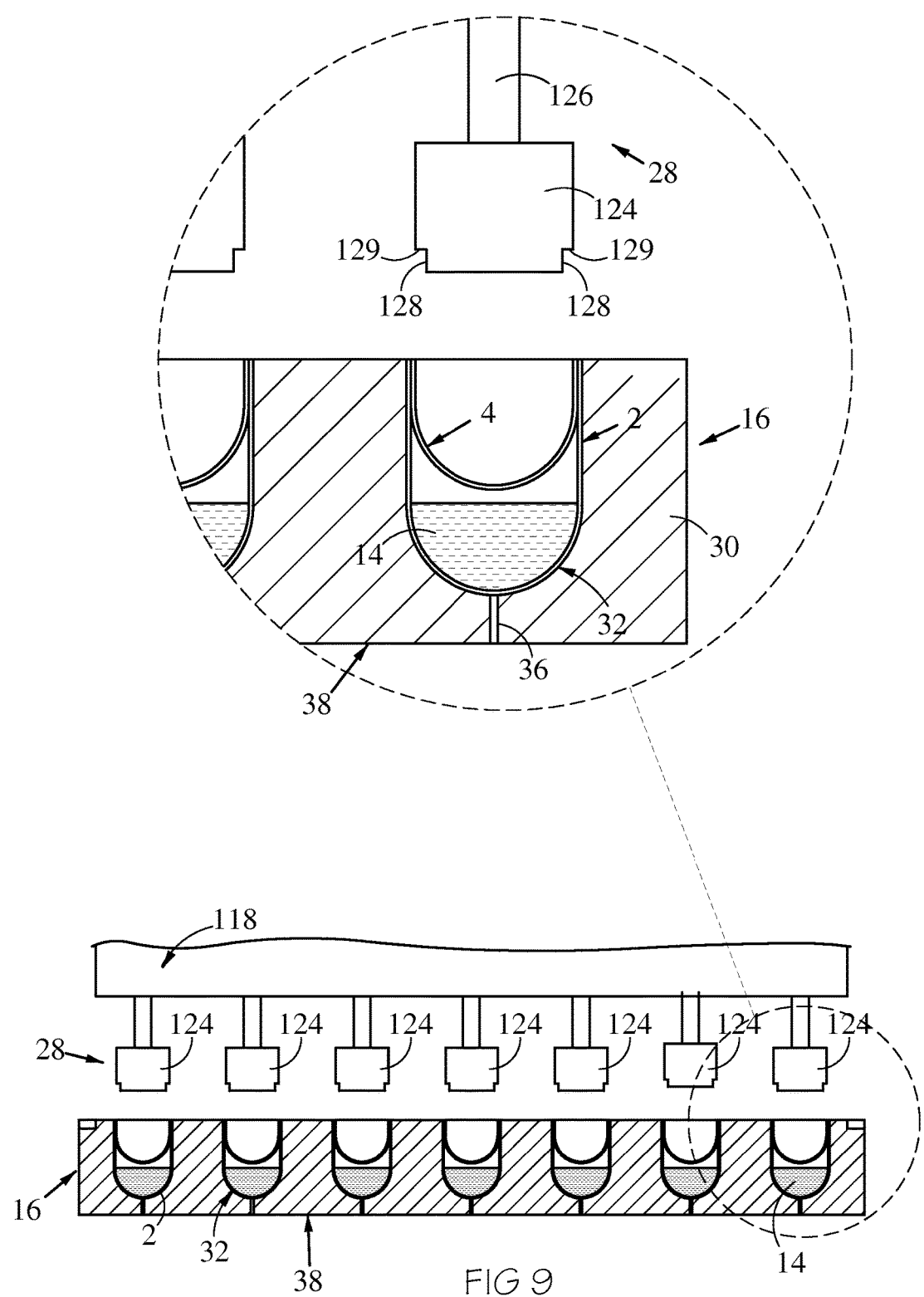
FIG. 9 shows a fragmentary sectional side view of a capsule bonding assembly of the apparatus of FIG. 3, illustrated in a raised position.
Figure 10:
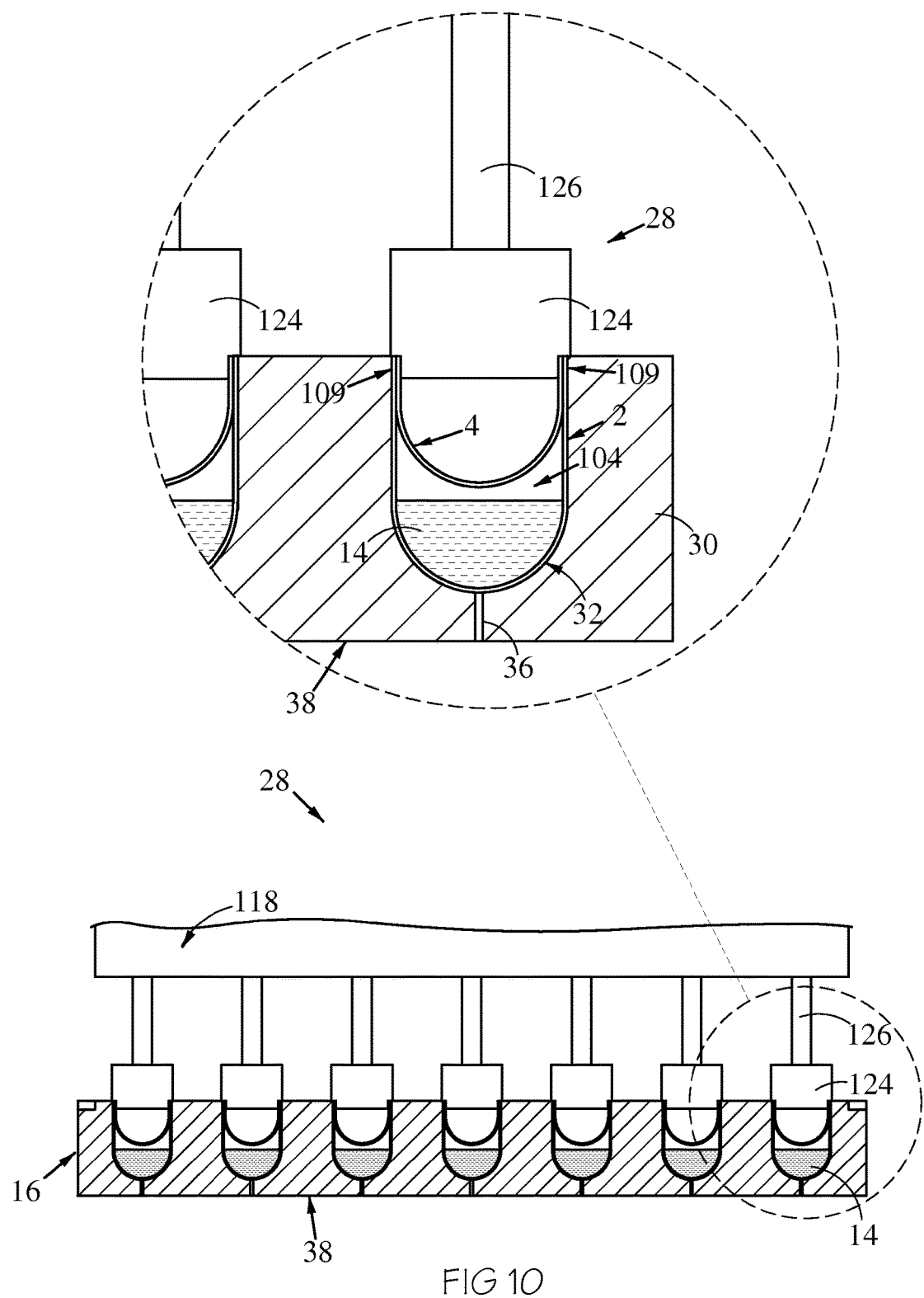
FIG. 10 shows a fragmentary, sectional side view of the capsule bonding assembly of FIG. 9, illustrated in a lowered position.

With reference to FIGS. 3, 9 and 10 of the drawings, the capsule bonding assembly 28 comprises a capsule bonding head 118, a support structure 120 for supporting the capsule bonding head 118 and a hydraulic heating mandrel actuator 122. The capsule bonding head 118 has forty two capsule bonding elements in the form of heating mandrels 124 mounted to lower ends of rods 126 which project from a lower end of the bonding head 118, as shown in FIGS. 9 and 10 of the drawings. The heating mandrels 124 are spaced a predetermined distance apart from one another. More specifically, the spacing between the heating mandrels 124 corresponds with the spacing between the receptacles 32 of the aluminium plate 30 of the capsule support trays 16. More specifically, as illustrated in FIGS. 9 and 10 of the drawings, each heating mandrel 124 is located above a different one of the receptacles 32 of the capsule support tray 16. Each heating mandrel 124 has a generally cylindrical configuration as illustrated in FIGS. 9 and 10 of the drawings, and includes a diaphragm engaging formation 128 and an end engaging formation 129. The diaphragm engaging formation 128 is configured and dimensioned for engaging the inner side 102 of the diaphragm 4 and for applying heat and pressure to the diaphragm 4 when the diaphragm engaging formation 128 of the heating mandrel 124 is inserted through the open end 8 of the diaphragm 4, as illustrated in FIG. 10 of the drawings. The end engaging formation 129 is configured and dimensioned for engaging the substantially flush aligned open ends 6,8 of the capsule body 2 and the diaphragm 4, respectively, for applying heat and pressure to the open end 8 of the diaphragm 4 and the open end 6 of the capsule body 2 for bonding the open ends 6, 8 of the capsule body 2 and the diaphragm 4, respectively, to one another. The hydraulic heating mandrel actuator 122 is operable to displace the heating mandrels 124 between a raised position as shown in FIG. 9 of the drawings, wherein each heating mandrel 124 is spaced away from the capsule support tray 116 and a lowered position, wherein each heating mandrel 124 is inserted into an open end 7 of a diaphragm 4, as illustrated in FIG. 10 of the drawings.

In use, each heating mandrel 124 is heated to a temperature of between 100° C. to 120° C. (optimally 110° C.) and applied to the diaphragm 4 for a period of approximately five to ten seconds, as illustrated in FIG. 10 of the drawings. In use, the diaphragm engaging formation 128 of the heating mandrel 124 supports, forms and heat welds overlapping parts of the capsule body 2 and the diaphragm 4 to one another, so as to form a fused overlapping wall region 109, as shown in FIG. 10 of the drawings. The fused overlapping wall region 109 comprises between 0.8 mm and 1.5 mm of overlapping parts of the capsule body 2 and the diaphragm 4 which are heat welded to one another.

It will be appreciated that inner and outer sides of the capsule body 2 and the diaphragm 4 and the open ends 6, 8 thereof, are supported by the receptacles 32 and the diaphragm engaging formations 128 of the heating mandrels 124 during bonding of the overlapping parts of the diaphragm 4 and the capsule body 2 and during bonding of the aligned open ends 6, 8, as illustrated in FIG. 10 of the drawings. More specifically, as can be seen from FIG. 10 of the drawings, the diaphragm engaging formations 128 and the receptacles 32 together support inner and outer sides of overlapping parts of the capsule body 2 and the diaphragm 4, and support the ends 6, 8, when the capsule body 2 and the diaphragm 4 are heat welded to one another. The applicant believes that the supporting of the inner and outer sides of the capsule body 2 and the diaphragm 4 and the supporting of the open end 6, 8, during bonding the capsule body 2 and the diaphragm 4 to one another, is also advantageous to ensure proper and optimal alignment and orientation of the capsule body 2 and the diaphragm 4 relative to one another. The applicant has found that the supporting, as described hereinabove, ensures that the capsule 12 is properly formed and hermetically sealed. Furthermore, the applicant envisages that supporting the capsule body 12 and the diaphragm 4 during bonding, as described hereinabove, limits the possibility of distortion and/or collapse of the capsule body 2 and the diaphragm 4 during bonding.

It will also be understood that, in use, the nitrogen gas provided within the chamber 104 reduces concentrations of atmospheric oxygen within the chamber 104 and thereby reduces the rate of oxidation of the Omega-3 oil 14. Furthermore, by providing a sub-atmospheric gas pressure within the chamber 104, the possibility of the Omega-3 oil 14 seeping out of the chamber 104 is significantly reduced. In addition, the applicant has found that reducing the gas pressure within the chamber 104 to a pressure below atmospheric pressure, is particularly advantageous during bonding of the overlapping regions of the diaphragm and the capsule body to one another. In this regard, the applicant has found that during bonding, the mandrel 124 also heats up the Omega-3 oil 14 in the chamber 104, causing it to expand. As a result of this expansion, the pressure within the chamber 104 increases. To overcome this problem, the internal pressure within the chamber 104 is reduced to a pressure which is sufficiently below atmospheric pressure, such that, when heat and pressure are applied during bonding, the internal pressure within the chamber 104 remains below atmospheric pressure particularly after the expansion of the Omega-3 oil 14 due to heating of the diaphragm and capsule body. This ensures that the internal pressure within the chamber 104 is at or below atmospheric pressure after bonding, so as to ensure that the chamber 104 is not pressurised to a pressure above atmospheric pressure, so as to ensure an effective hermetic seal. This reduction of the pressure within the chamber 104, is thus beneficial as increased internal pressure within the chamber 104 is undesirable as it may compromise the sealing of the chamber 104. Furthermore, the applicant has found that reducing gas pressure within the chamber 104 to a pressure below atmospheric pressure, is also advantageous after bonding. More specifically, the applicant has found that users of the capsule 12 often store the capsules 12 in hot environments such as, for example, in their cars where ambient temperatures are increased. The applicant has found that reducing gas pressure within the chamber 104 when manufacturing the capsule to a pressure below atmospheric pressure specifically enables the capsules to be used in relatively hot environments which may increase pressure within the chamber 104. This ensures that the capsule body 2 and the diaphragm 4 are not pressurized by internal pressure within the chamber 104 to pressures above ambient pressure when ambient temperatures to which the capsules 12 are exposed rise to relatively higher levels. In this regard, it will be appreciated that it is likely that the hermetic seal will be compromised if internal pressure within the chamber 104 exceeds atmospheric pressure and remains at this higher pressure for an extended period of time.

The apparatus 10 further includes a support tray vacuum system (not shown) and an inserting rod vacuum system (not shown). The support tray vacuum system is operable to produce a partial vacuum within the internal passage 36 of the capsule support tray 16, so as to produce a suction in the lower end of the receptacles 32 for holding the capsule bodies 2 in position within the receptacles 32 when withdrawing the mandrels 88 and the heating mandrels 124 from the diaphragms 4, in use. The inserting rod vacuum system is operable to produce a partial vacuum within the internal passage 91 of the diaphragm inserting rods 90 and the internal passage 89 of the mandrels 88, so as to produce a suction at a lower end of each mandrel 88 for holding the diaphragms 4 in position on each mandrel 88, in use.

Figure 2:
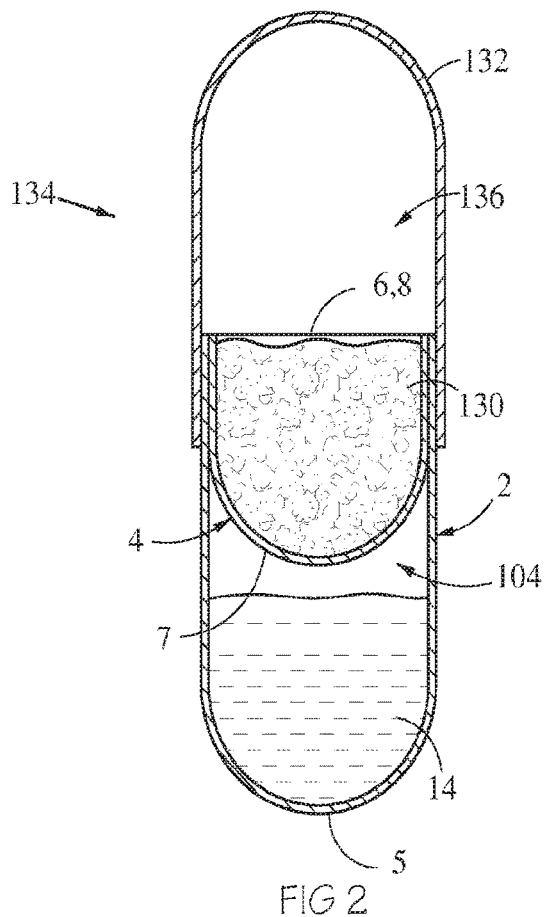
FIG. 2 shows a sectional side view of another embodiment of a capsule produced in accordance with the method of manufacturing a capsule, in accordance with the first aspect of the invention.

The applicant envisages that the capsule 12 may be used in particular applications wherein a capsule is required to hold an additional substance such as, for example, a medicament 130, which is required to be held apart from the Omega-3 oil 14 contained within the chamber 104. More specifically, the diaphragm 4 of the capsule 12 is filled with the medicament 130 and the capsule 12 is capped, as illustrated in FIG. 3 of the drawings, using a conventional capsule capping and filling machine which is used to cap known conventional capsule bodies with known conventional caps 132, so as to form a capsule 134 as shown in FIG. 2 of the drawings, each capsule 134 having an additional chamber 136 within which the medicament 130 is contained. Alternatively, the applicant envisages that in certain circumstances, the capsules 12 and the caps 132 will be supplied to a customer of the applicant, thereby permitting the applicant's customer to fill and cap the capsule 12, with a desired substance contained in the additional chamber 136, using the customers own conventional capsule capping and filling machine.

It will also be appreciated that it is extremely important that the shape and/or dimensions of the open ends 6, 8 of the capsule body 2 and the diaphragm 4 are maintained when the capsule body 2 and the diaphragm 4 are bonded to one another, particularly so as to permit the cap 132 to fit snugly, as shown in FIG. 2 of the drawings. Furthermore, the manner in which the capsule body 2 and the diaphragm 4 is supported, as described hereinabove, is extremely important to ensure that the shape and dimensions of the capsule 12 are maintained so as to permit the capsule 12 to be fed through conventional capsule capping and filling machines, which, due to their high speed and precision of operation, can only process capsules having precise and uniform shapes and dimensions. More specifically, the applicant has found that the supporting of the open ends 6, 8 of the capsule body 2 and the diaphragm 4, respectively, ensures that the open ends 6, 8 maintain a circular shape when viewed in end view, which is particularly important to ensure a snug fit between the capsule 12 and the cap 132 and to ensure that the shape and dimension of the capsule 12 is maintained, for the reasons set out above.

The applicant envisages that the digestible capsule 134 is advantageous for containing two substances, such as, the Omega-3 oil 14 and the medicament 130, which particularly must be held in separate chambers apart from one another. As such, other substances other than the Omega-3 oil 14 and the medicament 130 may be held in the chamber 104 and the additional chamber 136. The applicant furthermore envisages that the capsule 134 is particularly suitable for holding a wet and a dry composition, wherein the wet composition is in a liquid state, and, as such, is required to be held in a hermetic sealed chamber so as to prevent the liquid from leaking out of the hermetically sealed chamber. The applicant envisages that the capsule 134 is furthermore advantageous for holding two compositions which must be separated from one another so as to prevent degradation and/or reaction and/or contamination of one or both of the compositions. In particular, the applicant envisages that the capsule 134 is advantageous for holding a pharmacological composition in one of the chambers 104,136 and a natural composition in the other one of the chambers 104,136.

It will be appreciated that the exact configuration of the apparatus 10 used in accordance with the method of the invention, may vary greatly whilst still incorporating the essential features of the method of the invention as described hereinabove. Further the apparatus 10 may implement a method other than the method in accordance with the invention and similarly the method in accordance with the invention may be implemented on an apparatus other than the apparatus 10 described hereinabove.

The applicant envisages that the capsule body 2, the diaphragm 4 and the cap 132 are formed in accordance with known manufacturing procedures for forming hard gelatine capsules.

The applicant also envisages that the apparatus 10 and the method in accordance with the invention may be used to manufacture other types of capsules other than the digestible capsules 12 and 134 described hereinabove. More specifically, the applicant envisages that a capsule (not shown) may be produced by the method and/or by the apparatus which is configured for containing two part compositions which are required to be separated from one another, such as, for example, highly reactive or explosive substances, or, alternatively, two part adhesives.

In another embodiment of the invention (not shown), the apparatus includes a combined diaphragm inserting and capsule bonding assembly which replaces the diaphragm inserting assembly 24 and the capsule bonding assembly 28. The combined diaphragm inserting and capsule bonding assembly (not shown) is located with the vacuum chamber 56. As such, both the insertion of the diaphragm 4 into the capsule body 2, as hereinabove described, and the bonding of the capsule body 2 and the diaphragm 4 to one another, as hereinabove described, occurs within the controlled gaseous environment of the vacuum chamber 56.

The invention claimed is:

1. A method for manufacturing a capsule for holding a substance to be held in hermetic isolation, comprising:
   providing a first capsule portion of flexible material for holding the substance, the first capsule portion having a closed end, an opposed open end and a predetermined length defined therebetween;
   providing a second capsule portion of flexible material having a closed end, an opposed open end and a predetermined length defined therebetween, which is shorter than the length of the first capsule portion;
   at least partially filling the first capsule portion with the substance;
   inserting the closed end of the second capsule portion into the open end of the first capsule portion until the open ends of the first capsule portion and the second capsule portion are aligned substantially flush with one another and such that a region of the second capsule portion overlaps a region of the first capsule portion to close off the open end of the first capsule portion and define a chamber within which the substance is held;

bonding the substantially flush aligned open ends of the first capsule portion and the second capsule portion to one another to hermetically seal the chamber after inserting the closed end of the second capsule portion into the open end of the first capsule portion;

at least partially filling the second capsule portion with an additional substance; and securing a cap to the first capsule portion to define an additional chamber within which the additional substance is held, wherein the cap is secured to the first capsule portion after bonding the substantially flush aligned open ends of the first capsule portion and the second capsule portion to one another.

2. The method as claimed in claim 1, further including supporting the open ends of the first capsule portion and the second capsule portion while bonding the substantially flush aligned open ends of the first capsule portion and the second capsule portion to one another.

3. The method as claimed in claim 2, further including supporting inner and outer sides of the first and second capsule portions at an open end region adjacent the substantially flush aligned open ends of the first capsule portion and second capsule portion.

4. The method as claimed in claim 1, wherein the substantially flush aligned open ends of the first capsule portion and the second capsule portion are bonded to one another by applying heat and pressure to the open ends of the first and second capsule portions to fuse the open ends of the capsule portions to one another.

5. The method as claimed in claim 1, further including bonding the overlapping regions of the first capsule portion and the second capsule portion to one another.

6. The method as claimed in claim 5, wherein the overlapping regions are bonded to one another by applying heat and pressure to the overlapping regions.

7. The method as claimed in claim 6, further including:
providing a gas-tight chamber and providing a controlled gaseous environment within the gas-tight chamber;
locating the first and second capsule portions within the gas-tight chamber; and
inserting the closed end of the second capsule portion into the open end of the first capsule portion while the first and second capsule portions are located within the gas-tight chamber.

8. The method as claimed in claim 7, further including:
providing a non-toxic gas environment within the gas-tight chamber; and
inserting the closed end of the second capsule portion within the first capsule portion while the capsule portions are located within the non-toxic gas environment.

9. The method as claimed in claim 7, wherein a partial vacuum is applied to the gas-tight chamber to reduce gas pressure within the gas-tight chamber to a sub-atmospheric pressure when inserting the closed end of the second capsule portion into the open end of the first capsule portion.

10. The method as claimed in claim 1, wherein the first capsule portion comprises a cylindrical body which defines the open end and the closed end, the closed end being dome-shape.

11. The method as claimed in claim 1, wherein the second capsule portion comprises a cylindrical body which defines the open end and the closed end, the closed end being dome-shape.

12. The method as claimed in claim 1, wherein the first capsule portion and the second capsule portion are both formed of digestible material.

13. The method as claimed in claim 1, wherein the first capsule portion, the second capsule portion and the cap are formed of digestible material.

14. An apparatus for manufacturing a capsule, comprising:
a capsule receiver including at least one capsule receiving formation configured to receive therein a first capsule portion of flexible material for holding the substance therein, the first capsule portion having a closed end, an opposed open end and a predetermined length defined therebetween;
a capsule filling assembly including one or more nozzles for dispensing the substance, being operable to at least partially fill the first capsule portion which is supported, in use, by the capsule receiver;
a capsule handler including at least one capsule handling formation configured to handle a second capsule portion of flexible material having a closed end, an opposed open end and a predetermined length defined therebetween, which is shorter than the length of the first capsule portion, the capsule handler being displaceable between:
a first condition wherein the capsule handling formation is spaced apart from the capsule receiving formation; and
a second condition wherein the capsule handling formation is operable to insert a closed end of the second capsule portion handled thereby within the first capsule portion received by the capsule receiving formation until the open ends of the first and second capsule portions are aligned substantially flush with one another and such that a region of the second capsule portion overlaps a region of the first capsule portion closing off the open end of the first capsule portion to form an assembled capsule defining a chamber within which the substance is held; and
a capsule bonding assembly comprising a bonding head that directly engages and bonds the substantially flush aligned open ends of the first capsule portion and the second capsule portion of each assembled capsule to one another to hermetically seal the chamber.

15. The apparatus as claimed in claim 14, wherein the capsule receiving formation is configured for supporting an open end region of the first capsule portion defined adjacent the open end of the first capsule portion.

16. The apparatus as claimed in claim 14, wherein the capsule handling formation is configured to be inserted through the open end of the second capsule portion for supporting an open end region of the second capsule portion defined adjacent the open end of the second capsule portion.

17. The apparatus as claimed in claim 14, wherein the bonding head applies heat and pressure to the first and second capsule portions of the assembled capsules thereby bonding the first and second capsule portions to one another.

18. The apparatus as claimed in claim 17, wherein the bonding head defines an end engaging formation configured to engage directly the substantially flush aligned open ends of the first and second capsule portions to apply heat and pressure to the open ends thereby bonding the open ends of the first and second capsule portions to one another.

19. The apparatus as claimed in claim 18, wherein the bonding head has a second capsule engaging formation configured to engage the inner side of the second capsule portion to apply heat and pressure to the second capsule portion to bond the overlapping regions of the first and second capsule portions to one another.

20. The apparatus as claimed in claim 14, further including a gas-tight chamber within which the first and second capsule portions are located when inserting the second capsule portion into the first capsule portion when forming an assembled capsule to achieve a controlled gaseous environment within the chamber of the assembled capsule.

21. The apparatus as claimed in claim 20, further including a vacuum device which applies a partial vacuum to the gas-tight chamber to reduce gas pressure within the gas-tight chamber to a sub-atmospheric pressure.

* * * * *